(12) United States Patent
Cheng

(10) Patent No.: US 6,911,051 B2
(45) Date of Patent: Jun. 28, 2005

(54) ROTATING PNEUMATIC KNEE JOINT STRUCTURE

(76) Inventor: Chia Pao Cheng, PO Box 82-144, Taipei (TW)

(*) Notice: Subject to any disclaimer, the term of this patent is extended or adjusted under 35 U.S.C. 154(b) by 40 days.

(21) Appl. No.: 10/640,059

(22) Filed: Aug. 14, 2003

(65) Prior Publication Data
US 2005/0038523 A1 Feb. 17, 2005

(51) Int. Cl.⁷ .............................. A61F 2/64; A61F 2/68
(52) U.S. Cl. ...................................................... 623/44
(58) Field of Search ............................ 623/44–46, 39, 623/40–43; 901/19, 25, 26

(56) References Cited

U.S. PATENT DOCUMENTS

| | | | | |
|---|---|---|---|---|
| 3,851,337 A | * | 12/1974 | Prahl | 623/49 |
| 4,064,569 A | * | 12/1977 | Campbell | 623/43 |
| 4,135,254 A | * | 1/1979 | Weber et al. | 623/43 |
| 4,846,842 A | * | 7/1989 | Connolly et al. | 623/43 |
| 5,704,945 A | * | 1/1998 | Wagner et al. | 623/44 |
| 5,704,946 A | * | 1/1998 | Greene | 623/44 |
| 5,728,172 A | * | 3/1998 | Krieger | 623/44 |
| 5,755,813 A | * | 5/1998 | Krukenberg | 623/44 |
| 5,888,212 A | * | 3/1999 | Petrofsky et al. | 623/24 |
| 5,899,943 A | * | 5/1999 | Shiraishi et al. | 623/44 |
| 5,904,721 A | * | 5/1999 | Henry et al. | 623/26 |
| 5,948,021 A | * | 9/1999 | Radcliffe | 623/44 |
| 6,086,616 A | * | 7/2000 | Okuda et al. | 623/44 |
| 6,113,642 A | * | 9/2000 | Petrofsky et al. | 623/24 |
| 6,117,177 A | * | 9/2000 | Chen et al. | 623/44 |
| 6,165,226 A | * | 12/2000 | Wagner | 623/39 |
| 6,355,071 B1 | * | 3/2002 | Cheng | 623/45 |
| 2002/0188355 A1 | * | 12/2002 | Chen | 623/45 |

* cited by examiner

Primary Examiner—Alvin Stewart
(74) Attorney, Agent, or Firm—Loeng C. Lei

(57) ABSTRACT

A rotating pneumatic knee joint structure is disclosed. The structure comprises a twisting connector module and a pneumatic module. The twisting connector module includes a rotating seat, an adjustable upper seat, adjustable screws, two rotating block modules, bearings, side-arch plate and axle, and screws and a plurality are used to lock all the components of the structure. A socket seat mounted at the thigh and a stop block within the rotating seat cause the lower limb connected to the pneumatic module to swing in a circular direction. Though the adjustable screw, and the spring support to hold the rotating block, the sole of the legs can be swing in a left or right direction so as to hold the weight of the user.

1 Claim, 6 Drawing Sheets

ROTATING PNEUMATIC KNEE JOINT STRUCTURE

BACKGROUND OF THE INVENTION (a) Technical Field of the Invention

The present invention relates to knee joint structure, and in particular, to a knee joint structure mounted to the amputated region of the thigh. The knee joint structure is provided with twisting and rotating device allowing the disabled to walk normally and naturally.

(b) Description of the Prior Art

Conventional artificial knee joint structure can only provide bending and kneeing action and when waling on uneven ground, due to the weigh of the user exerted onto the knee joint structure, the thigh will withstand different pressure and an outward pulling force will form at the sleeve, and the thigh will swing outward and twisting. This will cause pain to the muscle at the rear section. In other words, conventional artificial knee joint structure cannot be adjusted to withstand the weight of the user and the various type of road surface. Accordingly, it is an object of the present invention to provide a rotating pneumatic knee joint structure, which mitigates the above drawback.

SUMMARY OF THE INVENTION

Accordingly, it is an object of the present invention to provide a rotating pneumatic knee joint structure comprising a twisting connector modules and a pneumatic module, wherein the twisting connector module includes a twisting connector, a rotating seat, an adjustable rotating upper seat, adjustable screws module including spring support, spring, spring leaf and adjustable screws, two rotating block module including a rotating block, spring block, axle, beaming and pad, upper and lower bearing, two side arch plates and axle and are mounted by using screws and a plurality of flat head screws, the twisting head includes a seat body having a shaft hole with corresponding mounting slot, one side of the seat body is provided with two corresponding protruded wing having shaft hole for arch plate, and a shaft hole for mounting the interlinking rod of the pneumatic body, the protruded wing is a sloping face and a recess for the anti-shock block and the other side of the protruded wing is through hole to the mounting slot; the shaft hole is provided with rotating block at the sides thereof and a bearing and a pad are mounted thereto, by means of an axle and the elastic block, the circular fastener is installed by a sleeve, and the bearing is positioned within the recess, after the rotating seat is mounted, a recess is provided at the protruded edge and a stopping block is provided corresponding to the recess, the upper section of the rotating seat is provided with a bearing, a pad and an upper seat, the lower section of the rotating seat is a bearing and is mounted to the inner edge with screw, and the rotating upper seat is mounted with screw, and the rotating connector module and the pneumatic body are mounted with the arch plates having holes, and the axle passes through the shaft hole and is then locked with screws, the through hole at the lower edge of the arch plate is locked to the pneumatic body such that the shaft hole of the interlining rod is mounted with the axle and is then locked with screw.

Yet another object of the present invention is to provide rotating pneumatic knee joint structure, wherein the structure allows a disabled person to walk normally and naturally.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENT

Figure 1:
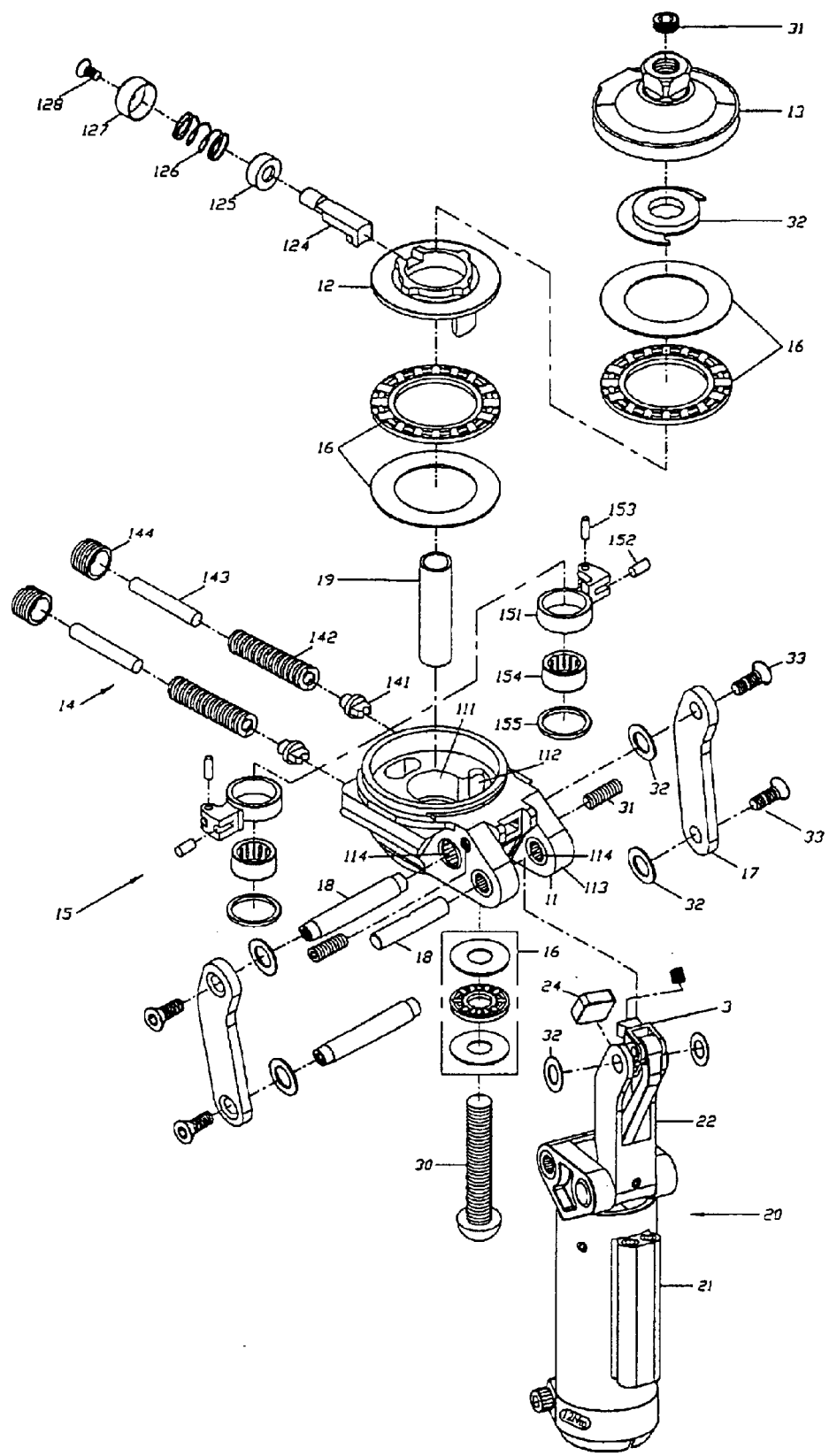
FIG. 1 is a perspective exploded view of a rotating pneumatic knee joint structure of the present invention.

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Referring to FIGS. 1 to 4A and 4B, there is shown a rotating pneumatic knee joint structure comprising a twisting connector module 10 and a pneumatic body module 20. The twisting connector module 20 includes a twisting connector 11, a rotating seat 12, an adjustable rotating upper seat 13, adjustable screws module 14 including spring support 141, spring 142, spring leaf 143 and adjustable screws 144, two rotating block modules 15 including a rotating block 151, a spring block 152, an axle 153, bearings 154 and pad 155, upper and lower bearings 16, two side arch plates 17 and axle 18 with screws 30, 31 and a plurality of pads 32 and flat head screws 33 fastening the components together.

The twisting connector 11 includes a seat body having a shaft hole 111 extended from the upper edge of the seat body, and the hole 111 are corresponding to the mounting slot 112 of the rotating block. One side of the seat body is provided with two corresponding protruded wings 113 having shaft boles 114 for the arch plate 17. The protruded wing 113 at the two sides is provided with a sloping face and a recess for the holding of anti-shock block 24 of the pneumatic body module 23. The other side of the protruded wing 113 is provided with two through screw holes 115 in communication with the mounting slot. The through screw hole 115 is provided with adjustable screw module 14. The spring support 141 is used to hold the axle 153 of the rotating block 151 and a spring 142 is used for the mounting. The spring 142 is provided with a spring leaf 143 and the adjustable screw 144 is then locked to the through screw hole at one side of the twisting connector.

In accordance with the present invention, the sleeve shaft hole 111 of the twisting connector 11 is provided with the rotating blocks 151 at the two sides thereof, and a rim fastener at the rotating block is mounted with bearing 144 and pad 155. The protruded edge at one side of the rim fastener is mounted with axle 153 and an elastic block 152. The rim fastener close to the center thereof is mounted with a sleeve 19 and the recess is used for the holding of the bearing 16. After that, the rotating seat 12 is mounted. The protruded side 121 at the upper portion of the rotating seat is a recessed port 122 and the lower corresponding side is extended to form a stop 123. The recessed port 122 passes through a moving block 124, which is mounted with a sleeve 125 and a spring 126, and a button cap 127 at the external of the spring. A cross-shaped head screw 128 is used for locking these components. The upper portion of the rotating seat is mounted with bearing 16, pad 32 and adjustable upper seat 13.

Finally, the lower section of the rotating seat is mounted with the bearing 16. A screw 30 is mounted at the inner edge of the sleeve and the upper section is used to adjust the upper seat using a stopping screw 30 which is locked to form as a unit.

Figure 2:
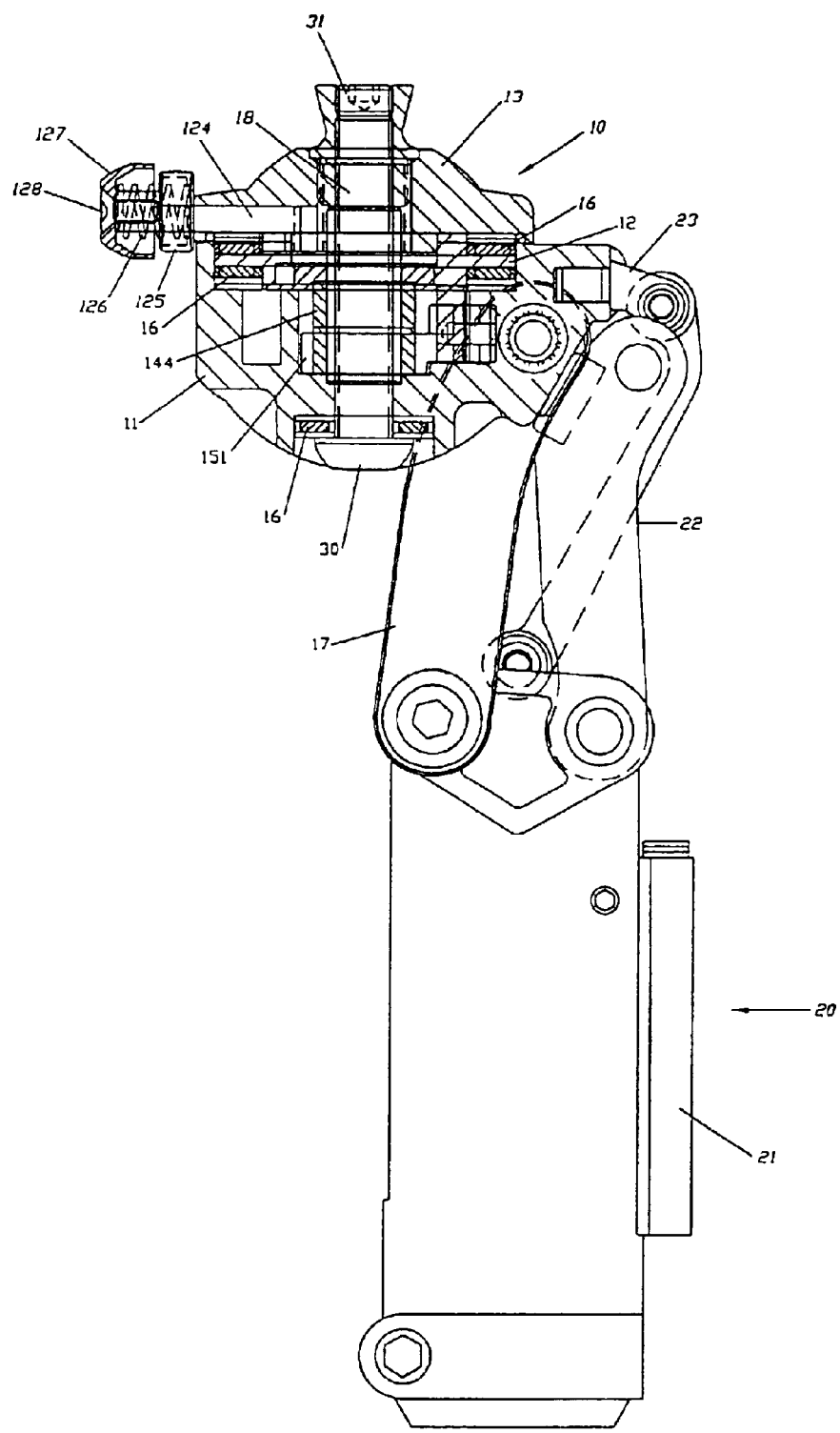
FIG. 2 is a top view of the rotating pneumatic knee joint structure of the present invention.
Figure 3:
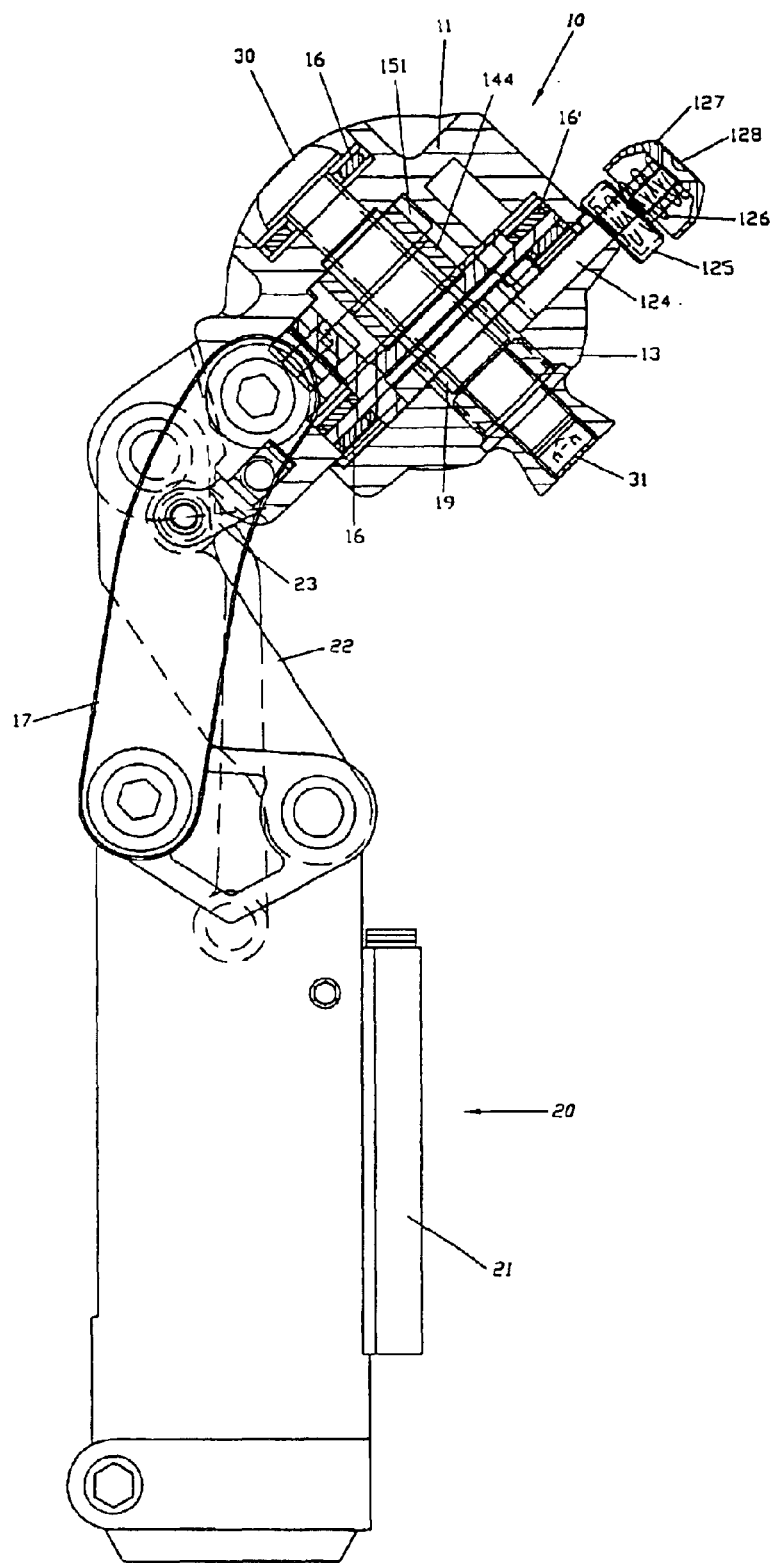
FIG. 3 is a top view of the rotating pneumatic knee joint structure, showing the bending process of the present invention.
Figure 4A:
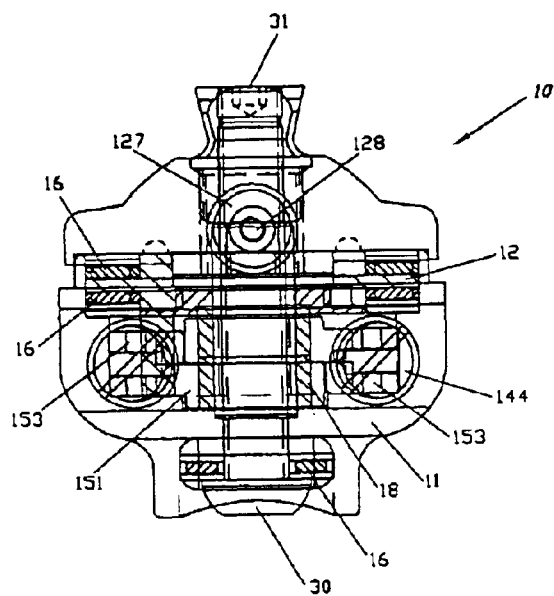
FIGS. 4A, 4B show front views and side views of the rotating pneumatic knee joint structure of the present invention.
Figure 4B:
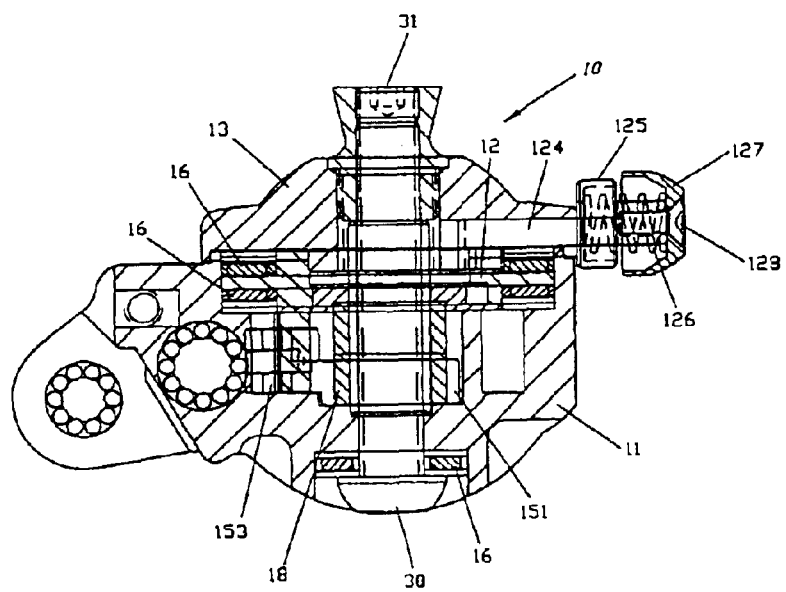

Lastly, the two lateral sides of the twisting connector module 10 and the pneumatic body 20 are provided with arch plate 17 having holes mounted with an axle 18 into the shaft hole 114 of the protruded wing 113. A screw 33 is used to lock the component. The through hole at the lower edge of the arch plate is locked to the pneumatic body 21. The shaft hole 114 of the interlinking rod 22 of the pneumatic body 21 is mounted with the axle 18 and a screw 33 is used to lock the component as one unit. A completed unit is shown in FIG. 2 and the angle of rotation is 135 degree.

Figure 5A:
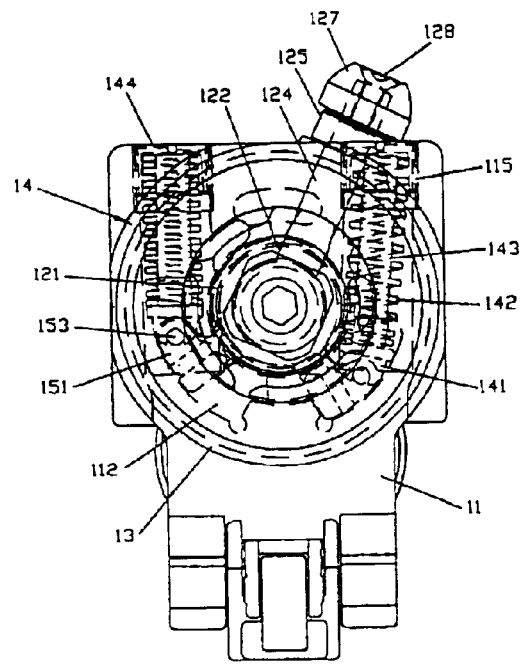
FIGS. 5A, 5B are schematic views showing the twisting state of the rotating pneumatic knee joint structure of the present invention.
Figure 5B:
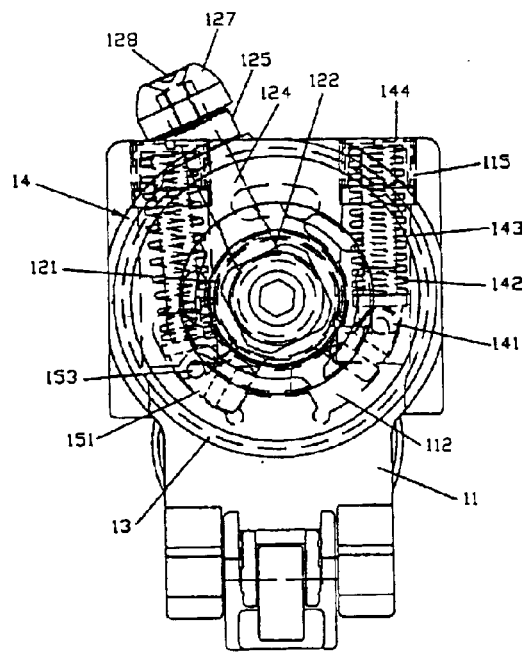

Referring to FIGS. 5A, 5B, there is shown the twisting of the structure in accordance with the present invention. After the mounting slot 112 is placed with the rotating block 151, and the rim fastener is also mounted with a sleeve 19, the axle 153 is urged by the spring support 141. The spring support is mounted with a spring 142 and a spring leaf 143. The screw hole 115 is locked with an adjustable screw 144 and the recess of the twisting connector is placed with a bearing 16 mounted with a rotating seat 12 such that the stopping block 123 at one side of the rotating seat is positioned at the center region of the two rotating protruded edge. The protruded edge of the rotating seat is placed with a bearing 16 and a pad 32. After the recess of the bottom section of the rotating seat is mounted with the bearing 16, screw 30 and the upper seat 13 are mounted with screw 31, and the recess 122 of the protruded edge side 121 is provided with a braking block 124 having externally mounted with a sleeve 125, which is urged by a spring 126. After a rotating button cap 127 is capped to the recess, a screw 128 is used for locking, as shown in FIG. 4.

When the braking block 124 is pressed, the engaging slot at the front edge of the block will be released from the recess 122 of the edge side 121 of the rotating seat so that the rotating upper seat 13 rotates to the left, and right and the stopping block 123 extended from the bottom section of the rotating seat is positioned at the center slot of the two rotating blocks 151, when one side is rotated, the screw module 14 will be compressed and therefore the left and right movement of the knee joint is obtained.

Figure 6A:
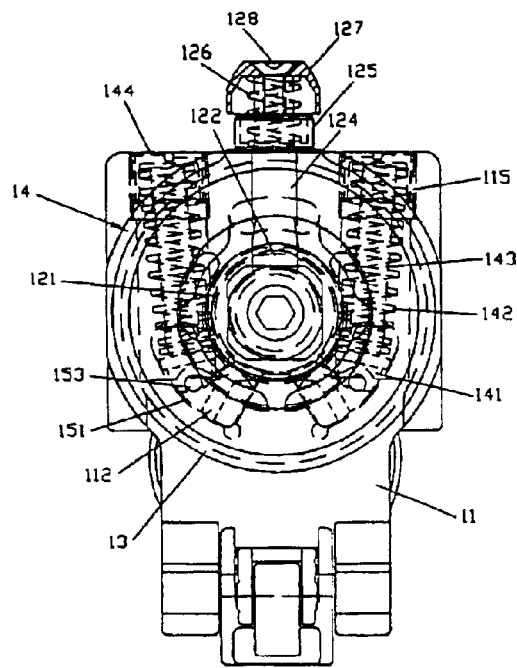
FIGS. 6A, 6B are schematic views showing left-right swinging of the rotating pneumatic knee joint structure of the present invention.
Figure 6B:
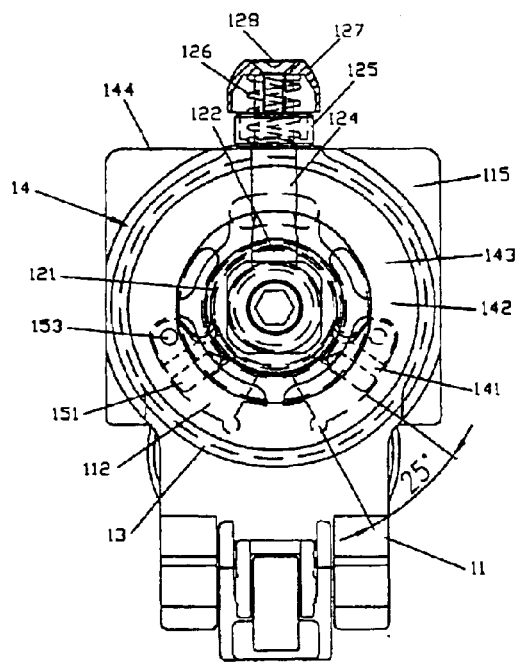

Referring to FIGS. 6A, 6B, there is shown the left and right swinging operation of the structure in accordance with the present invention. Before the braking block 124 is pressed, i.e., at a stagnant situation, the lower section of the main body of the knee joint is in a straight line, and after the rotating block fastening slot is mounted with the rotating block, the adjusting angle of the leg plate is between 25 degree, and the leg plate can be swung left and right in accordance with the contour of the landscape.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A rotating pneumatic knee joint structure comprising a twisting connector modules and a pneumatic module, wherein the twisting connector module includes a twisting connector, a rotating seat, an adjustable rotating upper seat, adjustable screws module including a spring support, a spring, a spring leaf and adjustable screws, two rotating block modules including a rotating block, a spring block, a first axle, bearings, a pad, upper and lower bearings, two side arch plates and a second axle which are mounted together by a plurality of flat head screws, the twisting head includes a seat body having a sleeve shaft hole with a corresponding mounting slot, one side of the seat body is provided with two corresponding protruded wings having shaft holes for the arch plates, an interlinking rod of the pneumatic module is fitted between the protruded wings, the protruded wings have a sloping face and a recess for an anti-shock block, and the other side of the protruded wings is provided with a through hole in communication with the mounting slot, the sleeve shaft hole of the twisting connector is provided with a rotating block at the sides thereof and a bearing and a pad are mounted thereto, by means of an axle and an elastic block, a recessed port is provided at a protruded edge and a stopping block is provided corresponding to the recessed port, an upper section of the rotating seat is provided with a bearing, a pad and an upper seat, the rotating upper seat is mounted with screw, and the twisting connector module and the pneumatic module are mounted with the arch plates having holes, and the axles pass through the shaft holes and are then locked with screws, the arch plates are locked to the pneumatic module.

* * * * *